United States Patent [19]

Stewart et al.

[11] Patent Number: 4,745,353
[45] Date of Patent: May 17, 1988

[54] IN SITU BS&W MEASUREMENT

[75] Inventors: Thomas L. Stewart, Houston; Florian C. Demny, Pasendana, both of Tex.

[73] Assignee: Shell Oil Company, Houston, Tex.

[21] Appl. No.: 780,521

[22] Filed: Sep. 25, 1985

[51] Int. Cl.[4] ............................................. G01N 23/04
[52] U.S. Cl. ................................ 324/58.5 A; 73/61 R
[58] Field of Search ............. 210/746, 96.1; 73/61 R, 73/61.1 R; 324/58.5 R–C, 57, 62, 431, 439

[56] References Cited

U.S. PATENT DOCUMENTS

| 2,532,817 | 12/1950 | Lafferty | 324/58.5 A |
|---|---|---|---|
| 3,034,046 | 5/1962 | Sasaki | 324/58.5 A |
| 3,060,421 | 10/1962 | Rideout | 324/58.5 A |
| 3,498,112 | 3/1970 | Howard et al. | |
| 3,956,695 | 5/1976 | Stamm | 324/58.5 A |
| 4,301,400 | 11/1981 | Paap | |
| 4,401,575 | 8/1983 | Stewart et al. | 210/746 |
| 4,543,191 | 9/1985 | Stewart et al. | |

FOREIGN PATENT DOCUMENTS

| 0032061 | 7/1981 | European Pat. Off. | |
|---|---|---|---|
| 1124461 | 8/1968 | United Kingdom | 324/58.5 A |
| 2045945 | 11/1980 | United Kingdom | |
| 2103803A | 2/1983 | United Kingdom | |
| 2110377A | 6/1983 | United Kingdom | |

OTHER PUBLICATIONS

Kalinski: "A Microwave Attenuation Comparator..." 5th European Microwave Conference—Sep. 1975—pp. 223–227.
Radio-Wave Interface Detector Measures Low, Oil & Gas Journal, Jan. 30, 1984, Technology pp. 150–152.
Agar Corporation, Energy Conservation & Pollution Control, 6.01.85 Agar Corp., Inc. 2215 Bauer Dr., Houston, Tex. 77080.

Primary Examiner—Reinhard J. Eisenzopf
Assistant Examiner—Jose M. Solis

[57] ABSTRACT

A centrifugal filter element is inserted into a pipeline to provide a dry oil stream for analysis. A moisture sensing probe is inserted along the central axis of the centrifugal filter to sense the properties of the dry oil stream therein. A second probe is inserted into the pipeline to sense the properties of the undried oil. Comparison of the output of the two probes reveals the water content of the oil in the pipeline.

4 Claims, 1 Drawing Sheet

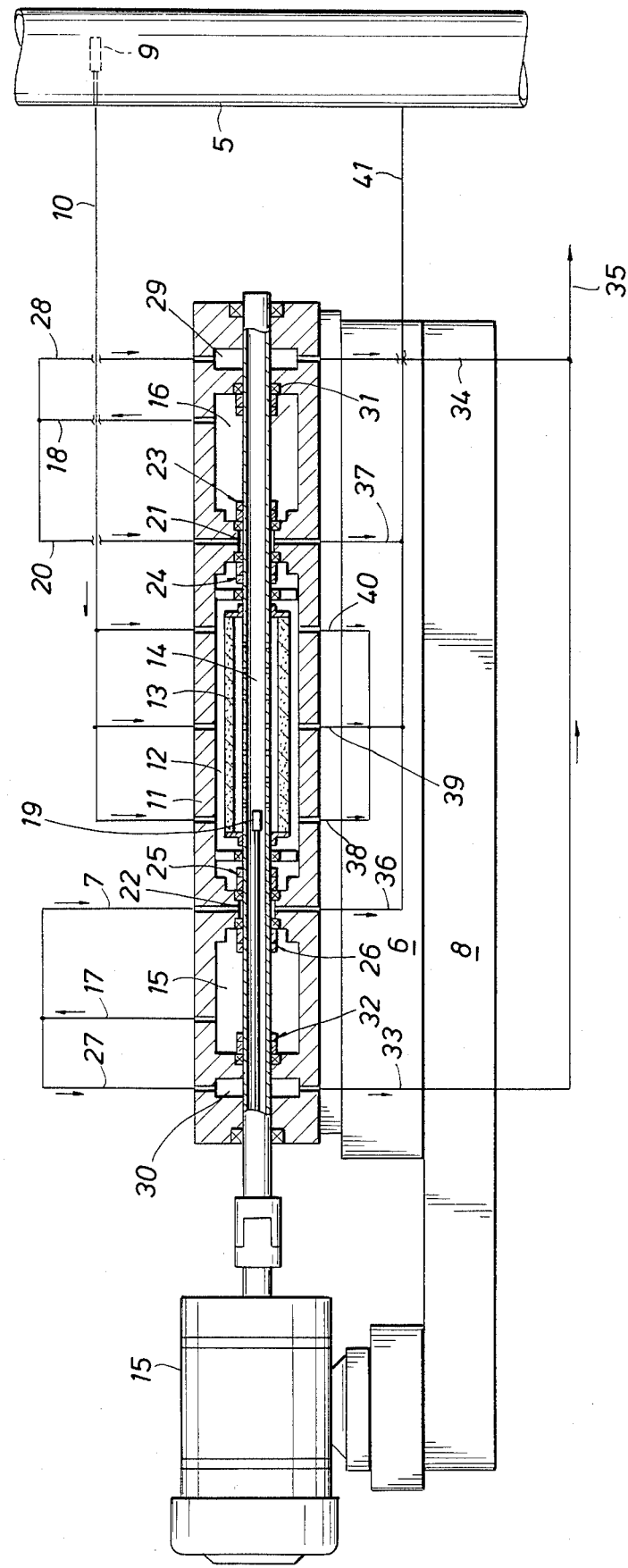

IN SITU BS&W MEASUREMENT

BACKGROUND OF THE INVENTION

A device for measurement of basic sediment and water (BS&W) in a predominantly non-aqueous stream (e.g. pipeline crude oil), is disclosed in U.S. Pat. No. 4,401,575. This device is an improvement on capacitance type instruments of the art which are dependent upon the extent to which the intrinsic dielectric constant of the subject fluid varies with time. The gravity and physical composition of crude oil are two factors which determine its intrinsic dielectric constant. If one or both of these properties should vary, instruments measure the accompanying change in the dielectric constant as percent BS&W. This yields an inaccurate measurement of BS&W because instruments must be initially set to read zero BS&W as the intrinsic dielectric constant of the fluid. The capacitance type instruments of the prior art have no means for automatically correcting the zero BS&W setting to compensate for periodic variations in the oil properties dimensions. By comparison, the device of U.S. Pat. No. 4,401,575 provides for automatic compensation of BS&W measurements by producing a clean, dry sample of the line fluid for measurement of its intrinsic dielectric constant. In this way, the true BS&W content of the fluid is measured by finding the difference between the dielectric constants of the wet and dry streams.

Even though the improvement over the prior art represented by the invention of U.S. Pat. No. 4,401,575 is substantial, it has now been discovered that an additional improvement can be made which even further increases the efficiency and accuracy of this invention. Thus, it has been discovered that substitution of another type of instrument for the capacitance type instrument of U.S. Pat. No. 4,401,575 avoids problems which exist where seals between the wet oil and dry oil chambers occasionally leak. In view of the extreme sensitivity of this device, any leakage, however small, can measurably reduce the accuracy of readings. While U.S. Pat. No. 4,401,575 takes one approach to reducing this problem, it has now been found desirable to provide an additional means which substantially eliminates problems with leakage from the wet oil chamber to the dry oil chamber.

SUMMARY OF THE INVENTION

The present invention provides a process and apparatus for measuring the basic water and sediment content of a wet stream which is predominantly non-aqueous, comprising, removing a sample of the wet stream, admitting the wet stream sample to an outer chamber containing an inner chamber having a wall formed of a filter, rotating the inner chamber while pressuring the wet stream sample from the outer chamber into the inner chamber, whereby any sediment present is filtered from the wet stream sample passing into the inner chamber and centrifugal force in the inner chamber forces water in the wet stream sample to remain in the outer chamber and thereby form a dry stream sample, producing short wave radio waves of a fixed frequency and constant energy, emitting the radio waves by an antenna into the dry stream sample and the wet stream or wet stream sample, determining the attenuation of the radio waves by the effect upon output voltage from the means producing the radio waves, and measuring the difference between the attenuation of the radio waves emitted into the dry stream sample and attenuation of the radio waves emitted into the wet stream or wet stream sample to facilitate determining the true water and sediment content of the wet stream.

BRIEF DESCRIPTION OF THE DRAWING

The FIGURE schematically shows the flow paths of various streams within the apparatus of the invention.

DESCRIPTION OF PREFERRED EMBODIMENTS

In accordance with the present invention, a process and apparatus are provided for incorporating the water-/oil emulsion separator in U.S. Pat. No. 4,401,575 into a complete system for determining basic water and sediment in crude oil, other hydrocarbons, or other substantially non-aqueous streams. This invention is particularly concerned with the capacitance measurement cells in U.S. Pat. No. 4,401,575 and provides an alternative means for measuring BS&W in the non-aqueous streams. Significant advantages are realized in utilizing the substitute devices inasmuch as the devices can be inserted into places where it is not possible to insert the capacitance cells of U.S. Pat. No. 4,401,575. In making the substitution, problems with leakage to which the invention of U.S. Pat. No. 4,401,575 were directed are either totally avoided or substantially minimized.

A sectional view of the apparatus of the present invention is provided in the FIGURE where flow streams are shown schematically. Crude oil or other fluid containing a small amount of water is taken from a pipeline 5 or other storage or transport via line 10. Preferably, a radio wave detector 9 measures water concentration in the oil or other non-aqueous fluid at about the spot where a sample is removed via line 10. The radio wave detector 9 is designed to detect low concentrations of water in oil or other non-aqueous fluids. A transmitter produces short wave radio waves of a fixed frequency and constant energy. This shortwave energy is emitted by an antenna to the fluid. The more this fluid attenuates the radio waves, the less the output voltage at the detector. High water cuts are reflected by minimal voltage output readings. Further description of the radio wave detector may be found in the Oil and Gas Journal, Jan. 30, 1984, pages 150–152, and brochures of the Agar Corporation relating to Agar OW-101 and OW-102 Water in Oil Monitors, both dated June 1, 1985. While it is preferred that instrument 9 be inserted into the pipeline to avoid problems of measurement, it is manifest that the instrument may be inserted into line 10 or any other location prior to the fluid being acted upon to separate the water therefrom. The non-aqueous fluid taken from pipeline 5 is then passed through housing 11 supported by structures 6 and 8, and then into wet oil chamber 12. From chamber 12, the wet oil is forced through filter 13 and into hollow drive shaft 14. Hollow drive shaft 14 and filter 13 are spun by a motor or other drive means 15. While the present invention is not limited to the following theory, it appears that the resulting centrifugal force substantially prevents the water and sediment capable of otherwise passing through filter 13, from entering hollow shaft 14, and any water or sediment that may enter shaft 14 is forced outwardly back into chamber 12. Dry fluid in hollow chamber 14 passes outwardly into dry oil chambers 15 and 16. Dry oil from chambers 15 and 16 then is passed via lines 17 and 18 and then via lines 7 and 20 into spaces 21 and 22 separating seals 23 and 24, and seals 25 and 26, respectively, which separate wet oil chamber 12 from dry oil chambers 15 and 16. An additional minor portion of the dry sample stream may be passed via lines 27 and 28 into spaces 29 and 30 which are adjacent outer seals 31 and 32. Spaces 29 and 30 are at atmospheric pressure, and accordingly, the dry oil therefrom is passed via lines 33, 34 and 35 to drain or disposal. Dry oil from spaces 21 and 22 is passed via lines 36 and 37 along with wet oil from lines 38, 39 and 40, back to the pipeline 5 or other storage or transport via line 41.

Radio wave detector 19 is preferably deployed centrally within hollow drive shaft 14 and measures the dry oil sample immediately as it is formed. This avoids any problems with leakage which may occur from seals 23 through 26, 31 and 32. While radio wave detector 19 could be employed further out in the hollow drive shaft 19, either closer to drive means 15 or to the other end of the apparatus, or even in chambers 15 or 16 or located in lines 17 or 18, it is preferable, because of the leakage problem experienced with the apparatus, to employ the detector in the location shown in the drawing, or at least close thereto.

While the present invention has been described principally in terms of crude oil and wet and dry streams of such crude oils, it will be apparent that the basic principles of the invention are adaptable to other processes and apparatus utilizing non-oil streams, where it is desirable to measure BS&W.

What is claimed is:

1. A process for measuring the water and sediment content of a wet stream which is predominantly non-aqueous, comprising:

removing a sample of the wet stream;

admitting the wet stream sample to an outer chamber containing an inner chamber having a wall formed of a filter;

rotating the inner chamber while pressuring the wet stream sample from the outer chamber into the inner chamber, whereby any sediment present is filtered from the wet stream sample passing into the inner chamber and centrifugal force in the inner chamber forces water in the wet stream sample to remain in the outer chamber and thereby form a dry stream sample;

producing short wave radio waves of a fixed frequency and constant energy;

emitting the radio waves by an antenna into the dry stream sample substantially immediately as the dry stream sample is formed and into a portion of the wet stream;

determining the attenuation of the radio waves by the effect upon output voltage from means producing the radio waves; and measuring the difference between the attenuation of the radio waves emitted into the dry stream sample and the wet stream portion to facilitate determining the true water and sediment content of the wet stream.

2. The process of claim 1 wherein the portion of the wet stream is the wet stream inside a pipeline.

3. An apparatus for measuring the water and sediment content of a wet stream which is predominantly non-aqueous, comprising:

means for removing a sample of the wet stream;

means for admitting the wet stream sample to an outer chamber containing an inner chamber having a wall formed of a filter;

means for rotating the inner chamber while pressuring the wet stream sample from the outer chamber into the inner chamber to form a dry stream sample;

means for producing short wave radio waves of a fixed frequency and constant energy;

means for emitting the radio waves by an antenna into the dry stream sample substantially immediately as the dry stream sample is formed and into a portion of the wet stream;

means for determining the attenuation of the radio waves by the effect upon output voltage from means producing the radio waves; and means for measuring the difference between the attenuation of the radio waves emitted into the dry stream sample and the portion of the wet stream to facilitate determining the true water and sediment content of the wet stream.

4. The apparatus of claim 3 wherein the portion of the wet stream is inside a pipeline carrying crude oil.

* * * * *